United States Patent [19]

Chikama

[11] Patent Number: 5,176,126
[45] Date of Patent: Jan. 5, 1993

[54] BENDING DEVICE

[75] Inventor: Toshio Chikama, Tokyo, Japan

[73] Assignee: Kabushiki Kaisha Machida Seisakusho, Tokyo, Japan

[21] Appl. No.: 594,059

[22] Filed: Oct. 9, 1990

[30] Foreign Application Priority Data

Oct. 13, 1989 [JP] Japan .................. 1-264964

[51] Int. Cl.⁵ ............................ A61B 1/00
[52] U.S. Cl. .............................. 128/4; 138/120; 604/95; 604/282
[58] Field of Search ............... 128/4, 657, 772; 604/95, 282; 138/118, 120, 110; 901/15

[56] References Cited

U.S. PATENT DOCUMENTS

| | | | |
|---|---|---|---|
| 2,748,803 | 6/1956 | Guarnaschelli | 138/120 |
| 3,060,972 | 10/1962 | Sheldon | 128/4 |
| 3,583,393 | 6/1971 | Takahashi | 128/4 |
| 4,108,211 | 8/1978 | Tanaka | 128/4 |
| 4,580,551 | 4/1986 | Siegmund et al. | 128/4 |
| 4,686,963 | 8/1987 | Cohen et al. | 128/4 |
| 4,834,069 | 5/1989 | Umeda | 128/4 |
| 5,005,558 | 4/1991 | Aomori | 128/4 |
| 5,106,381 | 4/1992 | Chikama | 604/282 |

FOREIGN PATENT DOCUMENTS 52-9274 2/1977 Japan .
55-10605 1/1980 Japan .

Primary Examiner—Stephen C. Pellegrino
Assistant Examiner—Ralph A. Lewis
Attorney, Agent, or Firm—Fish & Richardson

[57] ABSTRACT

A bending device for use in an endoscope, a catheter or the like includes a frame of a generally cylindrical shape, a limitation member and an operating wire. The frame has annular portions disposed respectively in planes substantially perpendicular to an axis of the frame, and the annular portions are juxtaposed in an axial direction of the frame. The limitation member is received in an internal space of the frame, and engaging recesses are formed in each of opposite lateral edges of the limitation member and juxtaposed in a longitudinal direction of the limitation member. The annular portions of the frame are engaged in the engaging recesses, so that any adjacent ones of the annular portions are spaced a predetermined distance from each other. The limitation member has a number of arcuate portions bulged generally perpendicularly to the direction of the length of the limitation member, and the arcuate portions are juxtaposed in the longitudinal direction of the limitation member. The limitation member is mounted on the frame in such a manner that the arcuate portions are resiliently deformed, so that the opposite lateral edges of the limitation member are urged away from each other and resiliently held against an inner periphery of each of the annular portions.

11 Claims, 3 Drawing Sheets

Fig. 6
Fig. 7
Fig. 8
Fig. 9
Fig. 10
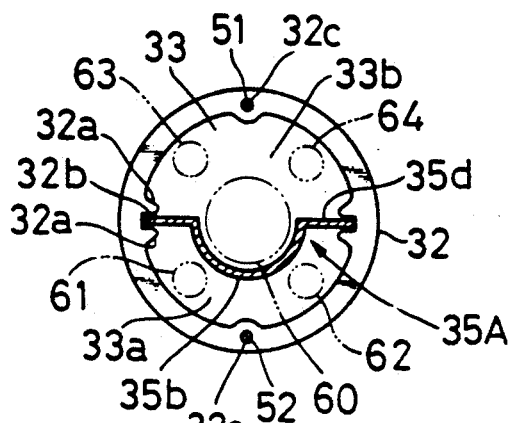
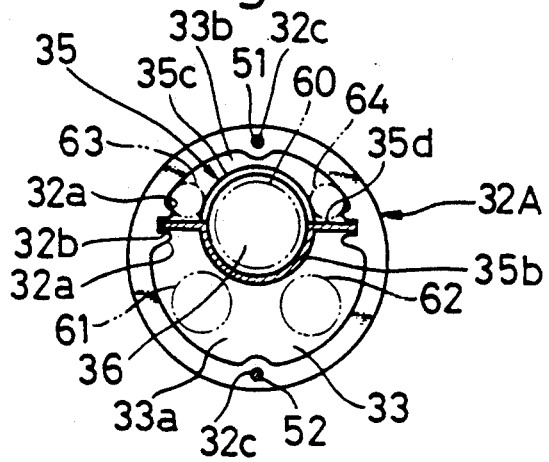
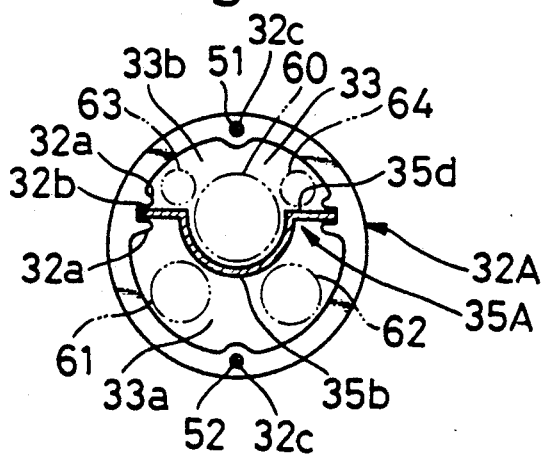
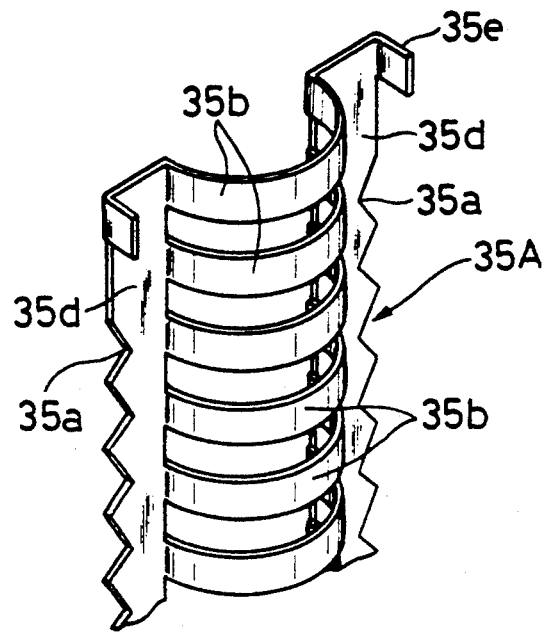
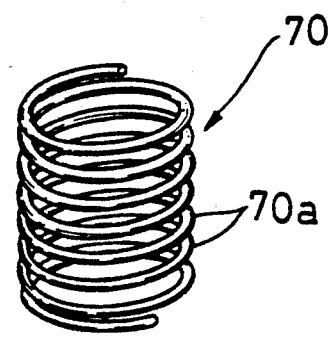

BENDING DEVICE

BACKGROUND OF THE INVENTION

This invention relates to a bending device for use, for example, in an endoscope.

As is well known, an endoscope comprises a hollow body, a flexible insertion portion extending from a front end of the body, a flexible bending portion extending from a distal end of the insertion portion, and a rigid portion provided at a distal end of the bending portion. An inspection window and an illumination window are formed at the rigid portion.

Japanese Utility Model Publication No. 9274/77 discloses a flexible tube structure for an endoscope which structure includes one coil serving as a frame, and a resilient thin plate serving as a limitation member for limiting deformation of the coil. FIG. 1 of Japanese Laid-Open (Kokai) Utility Model Application No. 10605/80 shows an example in which this flexible tube structure is applied to a bending portion of an endoscope. More specifically, in the bending portion, the resilient thin plate is received in an internal space defined by the coil and extends in the longitudinal direction of the coil. Recesses are formed in each of opposite lateral edges of the resilient thin plate, and are juxtaposed in the longitudinal direction of this plate. The turn portions of the coil are engaged in the recesses. The bending portion is bent in a direction perpendicular to the plane of the resilient thin plate by an operating wire, so as to direct an inspection window and an illumination window of the rigid portion toward a desired direction.

The above resilient thin plate performs two functions. The first function is to prevent the coil from being axially compressed (that is, to prevent the turn portions of the coils from moving toward one another) when pulling the operating wire, thereby ensuring a proper bending of the bending portion. The second function is to limit the direction of bending of the bending portion to a direction perpendicular to the plane of the resilient thin plate.

The above bending portion is simple in construction, and can be easily manufactured. However, when due to an external force applied to the coil, the coil is bulged or expanded radially outwardly in a direction passing through the diametrically-opposite portions of the coil engaged respectively with the opposite lateral edges of the resilient thin plate, the resilient thin plate sometimes is disengaged from the coil. In this case, when the coil is returned to its initial configuration upon removal of the external force, the resilient thin plate becomes engaged with the coil in such a manner that the former is displaced out of position with respect to the latter. When such displacement of the resilient thin plate with respect to the coil occurs, a smooth bending operation can not be effected, and a desired bending angle can not be obtained.

The above Japanese Laid-Open Utility Model Application No. 10605/80 shows, in FIGS. 3 to 8, examples in which a number of pieces of a circular cross-section are used as the limitation members. These pieces are received within the internal space of the coil, and are juxtaposed in the axial direction of the coil. Each of the pieces has recesses at each of its opposite sides, and the turn portions of the coil are engaged in the recesses of the piece. Referring to the example shown in FIG. 5 of this prior publication, each adjacent pieces are held in contact with each other only at their two portions, so that the pieces allow the coil to be bent only in a direction perpendicular to a plane including those portions of the pieces contacting with each other. This conventional construction also has a drawback that the turn portions of the coil may be disengaged from the recesses of the pieces.

SUMMARY OF THE INVENTION

It is an object of this invention to provide a bending device of the type in which a limitation member is positively prevented from being disengaged from a frame.

According to the present invention, there is provided a bending device comprising:

(a) a frame having a generally cylindrical shape and having an internal space therein, the frame having annular portions disposed respectively in planes substantially perpendicular to an axis of the frame, and the annular portions being juxtaposed in an axial direction of the frame;

(b) an elongated limitation member received in the internal space of the frame, engaging recesses being formed in each of opposite lateral edges of the limitation member and juxtaposed in a longitudinal direction of the limitation member in such a manner that the engaging recesses in one of the opposite lateral edges are generally in registry respectively with the engaging recesses in the other lateral edge to provide mating pairs, each of the annular portions of the frame being engaged in a respective one of the mating pairs of engaging recesses, so that any adjacent ones of the annular portions are spaced a predetermined distance from each other, the limitation member having a number of arcuate portions bulged substantially perpendicularly to the direction of the length of the limitation member, the arcuate portions being juxtaposed in the longitudinal direction of the limitation member, and the limitation member being mounted on the frame in such a manner that the arcuate portions are resiliently deformed, so that the opposite lateral edges of the limitation member are urged away from each other and resiliently held against an inner periphery of each of the annular portions; and (c) operating wire means for bending the frame and the limitation member, the operating wire means having a proximal end portion adapted to receive an operating force, the operating wire means having a distal end portion substantially fixed to a distal end portion of the frame.

BRIEF DESCRIPTION OF THE DRAWINGS

FIG. 6 is a view similar to FIG. 3, but showing another embodiment of the invention;

FIG. 7 is a perspective view of a portion of a limitation member used in the embodiment of FIG. 6;

FIGS. 8 and 9 are views similar to FIG. 3, but showing modified forms of the invention, respectively; and FIG. 10 is a perspective view of a further modified limitation member.

DESCRIPTION OF THE PREFERRED EMBODIMENTS OF THE INVENTION

A preferred embodiment of the invention will now be described with reference to the drawings.

Figure 1:
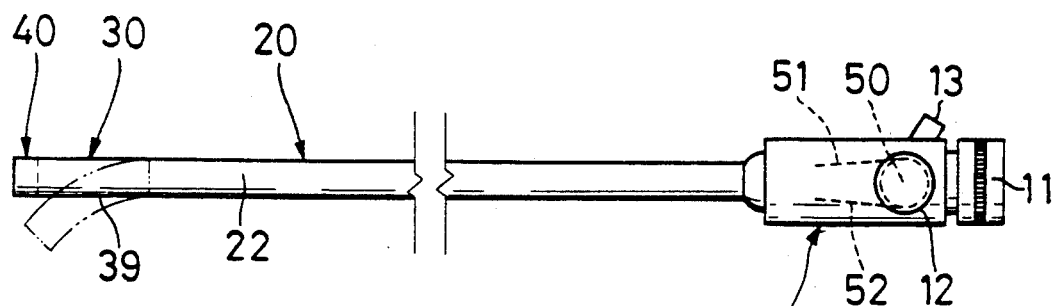
FIG. 1 is a schematic view of an endoscope incorporating a bending portion according to the present invention.

An endoscope shown in FIG. 1 comprises a hollow body 10, an insertion portion 20 extending from a front end of the body 10, a bending portion (bending device) 30 extending from a distal end of the insertion portion 20, and a rigid portion 40 provided at a distal end of the bending portion 30. Each of the insertion portion 20 and the bending portion 30 has a tubular shape, and is so flexible as to be bent.

An ocular tube 11 is mounted on the proximal end of the body 10, and a manipulation dial 12 is mounted on the peripheral wall of the body 10, and a forceps inlet portion 13 is formed on the peripheral wall of the body 10. A cable (not shown) is fixedly secured at one end to the peripheral wall of the body 10, and a connector (not shown) to be connected to a light source device is mounted on the other end of this cable.

The insertion portion 20 includes a holder coil (not shown) made from a strip or elongated narrow plate. A proximal end of this holder coil is fixedly secured to the body 10, and the distal end of the holder coil is connected to a connecting tube (not shown). A braid tube (not shown) is fitted on the holder coil, and a tube 22 (shown only in FIG. 1) made of a resin or rubber is fitted on the braid tube.

Figure 2:
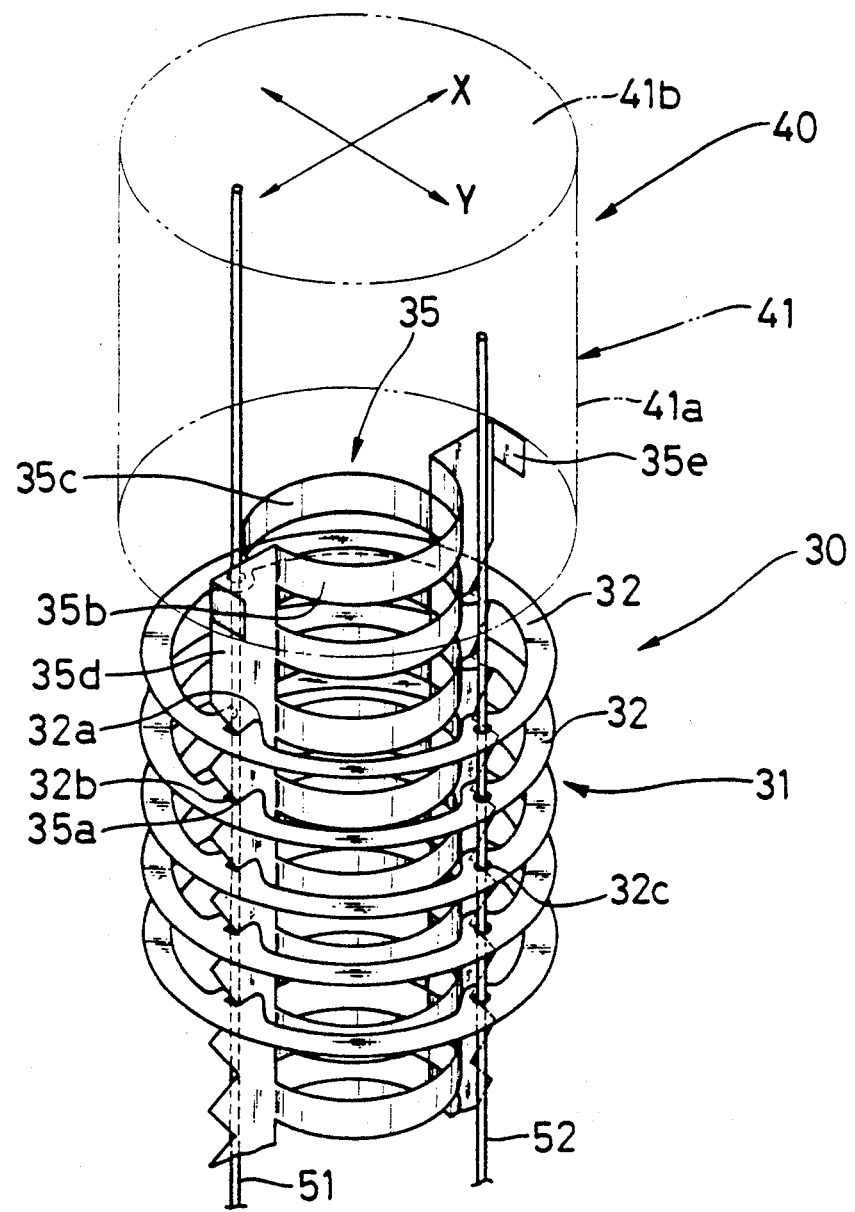
FIG. 2 is an enlarged perspective view of a portion of an internal structure of the bending portion.

FIG. 2 shows the bending portion 30 and the rigid portion 40. In FIG. 2, a direction X represents a direction perpendicular to the sheet of FIG. 1, and a direction Y represents an upward-downward direction in FIG. 1.

As shown in FIG. 2, the rigid portion 40 comprises a frame 41. The frame 41 has a cylindrical portion 41a, and an end wall 41b formed at a distal end of the cylindrical portion 41a. An forceps outlet, an inspection window, an illumination window, a water injection port, an air injection port are provided at the end wall 41b.

The forceps outlet provided at the rigid portion 40 is connected via a guide tube 60 (only shown in FIG. 3) to the forceps inlet portion 13 provided at the body 10. The guide tube 60 extends through the bending portion 30 and the insertion portion 20 into the body 10.

The ocular tube 11 is optically connected to the inspection window via an image transmitting system (not shown) including an optical fiber bundle 61 (only shown in FIG. 3) passing through the body 10, the insertion portion 20 and the bending portion 30. With this arrangement, inspection from the ocular tube 11 can be made.

Illumination light from the light source device is applied to the illumination window via an optical fiber bundle 62 (only shown in FIG. 3) passing through the above connector, the above cable, the body 10, the insertion portion 20 and the bending portion 30.

The water injection port is provided for injecting water to the inspection window so as to remove dirt therefrom. The water injection port is connected via a water feed tube 63 (only shown in FIG. 3) to a source of pressurized water disposed exteriorly of the endoscope. More specifically, the water feed tube 63 is connected at its one end to the pressurized water source, and extends through the wall of the body 10, and is passed through the body 10, the insertion portion 20 and the bending portion 30, and is connected at its other end to the water injection port.

The air injection port is provided for injecting compressed air to the inspection window so as to blow off the water deposited thereon. The air injection port is connected via an air feed tube 64 (only shown in FIG. 3) to a source of compressed air disposed exteriorly of the endoscope. More specifically, the air feed tube 64 is connected at its one end to the compressed air source, and extends through the wall of the body 10, and is passed through the body 10, the insertion portion 20 and the bending portion 30, and is connected at its other end to the air injection port.

The internal structure of the bending portion 30 will now be described in detail with reference to FIGS. 2 to 5. The bending portion 30 includes a frame 31 having a number of annular members 32, and a limitation member 35 for limiting the movement or displacement of the annular members 32.

Figure 3:
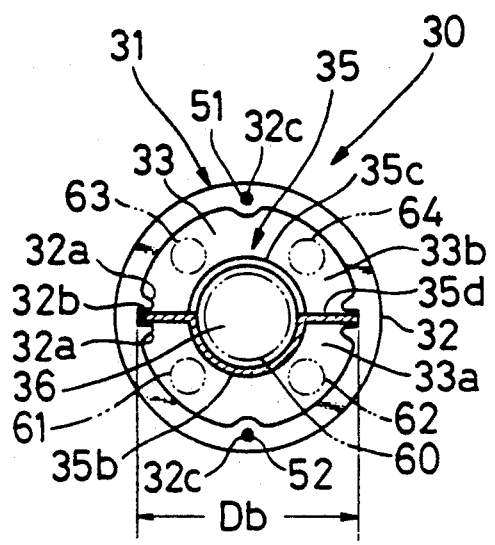
FIG. 3 is a transverse cross-sectional view of the internal structure of the bending portion.

The annular member 32 will now be first described. The annular member 32 is in the form of a ring-shaped (accurately circular) thin plate, as best shown in FIG. 3. Two pairs of projections 32a are formed respectively on diametrically-opposite portions of the annular member 32 and directed radially inwardly. A space between the pair of projections 32a serves as an engaging depression or recess 32b. A pair of insertion holes 32c are formed respectively through those diametrically-opposite portions of the annular member 32 circumferentially spaced 90° from the engaging depressions 32b.

Figure 4:
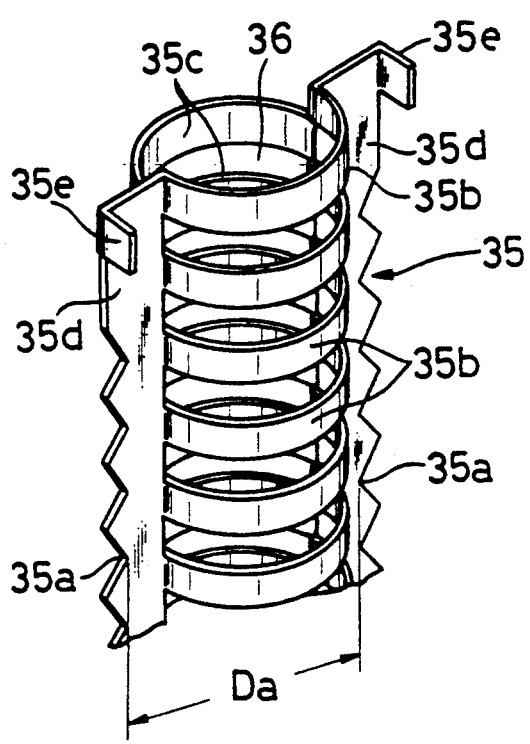
FIG. 4 is a perspective view of a portion of a limitation member.

Next, the limitation member 35 will now be described. As shown in FIG. 4, the limitation member 35 is formed by processing or working an elongated resilient thin flat plate of metal. More specifically, each of the opposite lateral edges of the resilient thin plate is serrated to provide a number of triangular engaging recesses 35a juxtaposed in the longitudinal direction of the resilient thin plate. Slits extending in the direction of the width of the resilient thin plate are beforehand formed therethrough, and are spaced from one another at predetermined intervals along the length of the resilient thin plate. Those portions of the resilient thin plate each lying between the adjacent slits are bent into a semi-circular shape alternately in opposite directions perpendicular to the plane of the resilient thin plate, thereby forming the limitation member 35. Therefore, the limitation member 35 has first and second arcuate portions 35b and 35c which are projected in opposite directions and arranged alternately in the direction of the length of the limitation member 35. The limitation member 35 has a pair of flat portions 35d defined respectively by its lateral side portions which have not been subjected to bending. The pair of flat portions 35d are disposed in a common plane, and are interconnected by the first and second arcuate portions 35b and 35c.

The first and second arcuate portions 35b and 35c are separate from one another in the longitudinal direction of the limitation member 35, and the first arcuate portions 35b projecting in the same direction are spaced from one another by a distance equal to the width of the second arcuate portion 35c. Similarly, the second arcuate portions 35c are spaced from one another by a distance equal to the width of the first arcuate portion 35b. Therefore, the limitation member 35 can be bent only in a direction perpendicular to the plane of the flat portions 35d, that is, in the upward-downward direction in FIG. 1 and in the direction Y in FIG. 2.

A pair of pawls 35e are formed on the distal end of the limitation member 35, and are fixedly secured to the inner peripheral surface of the cylindrical portion 41a of the frame 41 of the rigid portion 40. Also, another pair of pawls (not shown) are formed on the proximal end of the limitation member 35, and are connected to the above-mentioned connecting tube provided at the distal end of the insertion portion 20.

As shown in FIG. 2, the pair of engaging depressions 32b of each annular member 32 are engaged respectively with a corresponding pair of engaging recesses 35a formed respectively in the opposite lateral edges of the limitation member 35. Therefore, a number of annular members 32 are arranged in the longitudinal direction of the limitation member 35, and are prevented from being moved or displaced in this longitudinal direction. The thus arranged annular members 32 constitute the frame 31. The annular members 32 serve as annular portions of the frame 31. Each of the annular members 32 is disposed in a plane substantially perpendicular to the axis of the frame 31.

The distance Da (FIG. 4) between the bottoms of each pair of oppositely-disposed engaging recesses 35a in a natural condition of the limitation member 35 is greater than the distance Db (FIG. 3) between the bottoms of each pair of engaging depressions 32b in a natural condition of the annular member 32. The limitation member 35 is less in rigidity than the annular member 32. Therefore, when the annular members 32 and the limitation member 35 are assembled together, the annular members 32 are kept in substantially a natural condition whereas the limitation member 35 is resiliently contracted in the direction of the width thereof. This radial contraction is caused by such a resilient deformation of the limitation member 35 as to decrease the radius of curvature of the first and second arcuate portions 35b and 35c. As a result, the opposite lateral edges of the limitation member 35 tend to move away from each other, so that the bottom of each engaging recess 35a of the limitation member 35 is always held resiliently against the bottom of the corresponding engaging depression 32b of the annular member 32.

Figure 5:
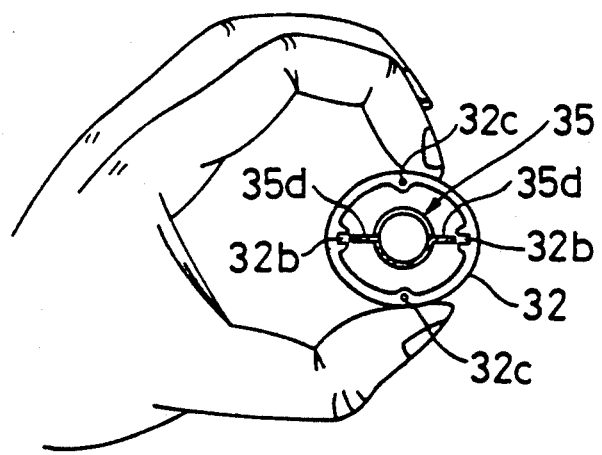
FIG. 5 is a plan view illustrative of the manner of attaching an annular member to the limitation member.

When each annular member 32 is to be attached to the limitation member 35, the annular member 32 is pressed with the fingers in a direction perpendicular to a line passing through the pair of engaging depressions 32b, so that the annular member 32 is deformed into an oval shape with the distance between the pair of engaging depressions 32b increased, as shown in FIG. 5. Subsequently, the limitation member 35 is passed through the annular member 32, and the pair of engaging depressions 32b are brought into registry respectively with the corresponding pair of engaging recesses 35a of the limitation member 35. Then, the fingers are released from the annular member 32, so that the engaging depressions 32a become engaged with the engaging recesses 35a, respectively.

The frame 31 has an internal space 33 of a circular cross-section surrounded by the annular members 32. The limitation member 35 is received within the internal space 33. The limitation member 35 has an auxiliary internal space 36 of a circular cross-section surrounded by the first and second arcuate portions 35b and 35c. The auxiliary internal space 36 is disposed coaxially with the internal space 33.

As shown in FIG. 3, the guide tube 60 for guiding the insertion of a forceps is received in the auxiliary internal space 36. The internal space 33 of the frame 31 is divided by the limitation member 35 into a pair of space portions 33a and 33b, and the optical fiber bundle 61 for inspection purposes and the optical fiber bundle 62 for illumination purposes are received in the space portion 33a. The water feed tube 63 and the air feed tube 64 are received in the other space portion 33b.

A braid tube, softer than the braid tube of the insertion portion 20, is fitted on the outer periphery of the frame 31, and a tube 39 (only shown in FIG. 1), softer than the tube 22 of the insertion portion 20, is fitted on the outer periphery of this braid tube.

Next, a mechanism for bending the bending portion 30 will now be described. This mechanism includes two operating wires 51 and 52. The operating wires 51 and 52 are fixedly secured to a peripheral surface of a pulley 50 mounted within the body 10, and extend forwardly from the upper and lower portions of the pulley 50, respectively. The pulley 50 is connected to the manipulation dial 12 via a shaft (not shown) extending through the peripheral wall of the body 10.

In the insertion portion 20, the operating wires 51 and 52 are passed respectively through a pair of guide tubes of a small diameter. Each of these guide tubes is formed by spirally winding a wire, and is received within the above-mentioned holder coil. The proximal ends of the guide coils are fixedly secured respectively to diametrically-opposite portions of the body 10 (that is, opposed upper and lower portions of the body 10 in FIG. 1), and the distal ends of the guide coils are fixedly secured respectively to diametrically-opposite upper and lower portions of the inner peripheral surface of the above-mentioned connecting tube.

As shown in FIG. 2, in the bending portion 30, the operating wires 51 and 52 are passed through the pair of insertion holes 32c of each annular member 32, and are fixedly secured at their distal ends respectively to diametrically-opposite upper and lower portions (FIG. 1) of the inner peripheral surface of the cylindrical portion 41a of the frame 41 of the rigid portion 40 by brazing. The positions of fixing of the distal ends of the operating wires 51 and 52, as well as the positions of fixing of the distal ends of the above guide coils, are circumferentially spaced 90° from the opposite lateral edges of the limitation member 35.

In the above construction, when the manipulating dial 12 is angularly moved in a counterclockwise direction (FIG. 1), the operating wire 52 is pulled, and the operating wire 51 is loosened. As a result, the bending portion 30 is bent downward. In contrast, when the manipulating dial 12 is angularly moved in a clockwise direction, the operating wire 51 is pulled, and the operating wire 52 is loosened. As a result, the bending portion 30 is bent upward.

During the bending of the bending portion 30, the limitation member 35 is bent in the direction Y in FIG. 2. The distance between those portions of the adjacent annular members 32 engaged with the limitation member 35 remain unchanged, and the distance between those portions of the adjacent annular members 32 disposed on one side of the limitation member 35 increases whereas the distance between those portions of the adjacent annular members 32 disposed on the other side of the limitation member 35 decreases.

During the bending of the bending portion 30, the annular members 32 interfere with one another, thereby maintaining the cross-section of the bending portion 30 in a substantially circular shape. Also, the interference of the annular members 32 with one another prevents the bending portion 30 from being bent only at one section thereof, thus ensuring a smooth bending.

When upon application of an external force to the bending portion 30, the annular member 32 is resiliently deformed into an oval shape in such a manner as to increase the distance between the diametrically-opposite portions of the annular member 32 engaged with the limitation member 35, the first and second arcuate portions 35b and 35c tend to be restored into their natural condition so as to increase their radius of curvature, so that the distance between the opposite lateral edges of the limitation member 35 is increased. As a result, the disengagement of the engaging depressions 32b of the annular member 32 from the engaging recesses 35a of the limitation member 35 is prevented. And besides, since the limitation member 35 and the annular member 32 are kept properly engaged with each other, that is, properly positioned with respect to each other, a smooth bending of the bending portion 30 can be always achieved.

In the bending portion 30, the guide tube 60 for the forceps is received in the auxiliary internal space 36 surrounded by the first and second arcuate portions 35b and 35c, and the guide tube 60 is always kept coaxially with the bending portion 30. Therefore, the operating force required for bending the bending portion 30 can be small. The reason for this will be described in the following.

Among the parts passed through the bending portion 30, the guide tube 60, particularly when the forceps is inserted thereinto, is most difficult to be bent. If the guide tube 60 is not disposed coaxially with the bending portion 30, the guide tube 60 is pulled to be displaced toward the axis of the bending portion 30, or is loosened to meander each time the bending portion 30 is bent. As a result, the guide tube 60 interferes with other parts received in the bending portion 30, and a frictional force resulting from such interference constitutes a resistance to the bending of the bending portion 30. In this embodiment, however, since the guide tube 60 is disposed coaxially with the bending portion 30, the guide tube 60 will not be displaced radially from the axis of the bending portion 30, thereby greatly reducing the resistance to the bending of the bending portion 30.

Further, since the guide tube 60 is bent in such a manner that it is supported by the first and second arcuate portions 35b and 35c arranged in the longitudinal direction of the limitation member 35, the guide tube 60 will not be bent at one portion thereof.

The first and second arcuate portions 35b and 35c of the limitation member 35 prevent the guide tube 60 from contacting with other parts in the bending portion 30, such as the optical fiber bundles 61 and 62.

In the bending portion 30, since the pair of operating wires 51 and 52 are guided respectively by the two rows of insertion holes 32c formed through the annular members 32, the operating wires 51 and 52 will not be displaced or moved into the internal space 33. Therefore, the operating wires 51 and 52 will not be brought into contact with the optical fiber bundles 61 and 62, the water feed tube 63 and the air feed tube 64, and hence will not damage these parts.

Other embodiments of the present invention will now be described. Those parts of such other embodiments corresponding respectively to those of the preceding embodiment are designated by identical reference numerals, respectively, and detailed explanation thereof will be omitted.

FIG. 6 and 7 shows another embodiment. A limitation member 35A used in this embodiment has only first arcuate portions 35b, and does not have the second arcuate portions 35c of the preceding embodiment. The arcuate portions 35b are arranged at equal intervals along the length of the limitation member 35A. When this limitation member 35A is used, the water feed tube 63 and the air feed tube 64 are not isolated from the guide tube 60 by the limitation member 35A, and these three tubes are all disposed in the same internal space 33b.

The limitation member 35A of FIG. 7 may be modified in such a manner that the arcuate portions 35b are closely spaced from one another by very narrow slits. In this case, the bending portion can be bent only in one direction, and only one operating wire is used.

FIG. 8 shows a modified annular member 32A. A pair of engaging depressions 32b are spaced equidistantly from each pair of insertion holes 32c, and are disposed closer to one of the two pairs of insertion hole 32c. In other words, a straight line passing through the pair of engaging depressions 32b is spaced from the axis or center of the annular member 32A. Therefore, the center of an imaginary cylindrical surface on which the first and second arcuate portions 35b and 35c are disposed is spaced or offset from the axis of the annular member 32A. One space portion 33a is greater than the other space portion 33b, and therefore the optical fiber bundles 61 and 62 passed through the space portion 33a can be thickened. In contrast with the illustrated example, a relatively thick water feed tube 63 and a relatively thick air feed tube 64 may be disposed in the space portion 33a.

FIG. 9 shows an example in which the annular members 32A of FIG. 8 are attached to the limitation member 35A of FIG. 6.

As shown in FIG. 10, a coil 70 may be used as the frame of the bending portion. In this case, opposed two sections of each turn portion 70a (annular portion) of the coil 70 are engaged respectively with the pair of mating engaging recesses 35a of the limitation member 35 or 35A.

The present invention is not to be restricted to the above embodiments, and various modifications can be made.

For example, in the embodiment shown in FIGS. 1 to 5, a bundle of wires for transferring electrical signals from a solid-state image-pickup device may be passed through the auxiliary internal space 36 surrounded by the first and second arcuate portions 35b and 35c of the limitation member 35. In this case, the solid-state image-pickup device is mounted on the rigid portion, and is optically connected to the inspection window.

In the above embodiments, although the annular member is made of a thin plate, it may be formed by a wire of a circular cross-section.

The width of the arcuate portion of the limitation member in the direction of the length of the limitation member may not be constant over the entire length of the arcuate portion. For example, the central section of the arcuate portion may be greater in width than the opposite end sections thereof, and the arcuate portion may have any other suitable shape.

The use of only one operating wire is possible, in which case the bending portion can be bent only in one direction.

The opposite lateral edges of the limitation member and the frame may be molded in a soft resin or rubber. In this case, the braid tube and the tube surrounding the frame are not necessary.

The present invention can be applied to the endoscope of the type in which the thickness or diameter of the insertion portion and the bending portion are very small, and further the present invention can be applied to a medical catheter.

What is claimed is:

1. A bending device comprising:
   (a) a frame having a generally cylindrical shape and having an internal space therein, the frame having annular portions disposed respectively in planes substantially perpendicular to an axial direction of said frame, and said annular portions being juxtaposed in the axial direction of said frame;
   (b) an elongated limitation member received in said internal space of said frame, engaging recesses being formed in each of opposite lateral edges of said limitation member in such a manner that said engaging recesses in one of said opposite lateral edges are generally in registry respectively with said engaging recesses in the other lateral edge to provide mating pairs, each of said annular portions of said frame being engaged in a respective one of said mating pairs of engaging recesses, so that adjacent ones of said annular portions are spaced a predetermined distance from each other, said limitation member having a plurality of arcuate portions disposed intermediate the opposite lateral edges of said limitation member, said arcuate portions being bulged substantially perpendicularly to the direction of the length of said limitation member, said arcuate portions being juxtaposed in the longitudinal direction of said limitation member, and said limitation member being mounted on said frame in such a manner that said arcuate portions are resiliently deformed, so that the opposite lateral edges of said limitation member are urged away from each other and resiliently held against an inner periphery of each of said annular portions, said limitation member comprising a single resilient thin plate and having a pair of flat portions disposed respectively adjacent to said opposite lateral edges of said resilient thin plate, said pair of flat portions disposed on a common plane and interconnected by said arcuate portions; and
   (c) operating wire means for bending said frame and said limitation member, said operating wire means extending along the longitudinal direction of said limitation member, said operating wire means having a proximal end portion adapted to receive an operating force, said operating wire means having a distal end portion substantially fixed to a distal end portion of said limitation member.

2. A bending device according to claim 1, in which said arcuate portions comprises first and second arcuate portions arranged alternately in the longitudinal direction of said limitation member, said first arcuate portions projecting in a first direction perpendicular to the plane of said flat portions, and said second arcuate portions projecting in a second direction which is opposite to said first direction and is perpendicular to the plane of said flat portions.

3. A bending device according to claim 1, in which said arcuate portions project in the same direction perpendicular to the plane of said flat portions, and are spaced from one another in the longitudinal direction of said limitation member.

4. A bending device according to claim 1, in which said frame has independent annular members of a circular shape which serve as said annular portions of said frame, respectively.

5. A bending device according to claim 4, in which each of said annular members is composed of a thin plate.

6. A bending device according to claim 5, in which two pairs of projections are formed on each of said annular members, and are spaced from each other circumferentially of said annular member, said two pairs of projections extending radially inwardly from said annular member, a space between each said pair of projections serving as an engaging depression, a bottom of each of said engaging recesses of said limitation member being resiliently held against a bottom of a respective one of said engaging depressions of said annular member.

7. A bending device according to claim 6, in which a line interconnecting said pair of engaging depressions of said annular member passes through an axis of said annular member.

8. A bending device according to claim 7, in which said arcuate portions comprises first and second arcuate portions arranged alternately in the longitudinal direction of said limitation member, said first arcuate portions projecting in a first direction perpendicular to the plane of said flat portions, said second arcuate portions projecting in a second direction which is opposite to said first direction and is perpendicular to the plane of said flat portions, an auxiliary space being formed by said first and second arcuate portions, said auxiliary space being disposed coaxially with said internal space, and said auxiliary space being adapted to receive an elongated part therein.

9. A bending device according to claim 6, in which a line interconnecting said pair of engaging depressions of said annular member is spaced from an axis of said annular member.

10. A bending device according to claim 6, in which said annular member has at least one insertion hole formed therethrough and disposed at a position spaced equidistantly from said pair of engaging depressions, said operating wire means being passed through said insertion hole.

11. A bending device according to claim 1, in which said frame is composed of a single coil having a number of turn portions juxtaposed in an axial direction of said coil, said turn portions serving as said annular portions, respectively.

* * * * *